United States Patent [19]

Pickens et al.

[11] Patent Number: 4,612,284

[45] Date of Patent: Sep. 16, 1986

[54] PROCESS FOR THE ENZYMATIC HYDROLYSIS OF NON-GELATINIZED GRANULAR STARCH MATERIAL DIRECTLY TO GLUCOSE

[75] Inventors: Carl E. Pickens, Decatur; Carl W. Niekamp, Forsyth, both of Ill.

[73] Assignee: A. E. Staley Manufacturing Company, Decatur, Ill.

[21] Appl. No.: 656,117

[22] Filed: Sep. 28, 1984

[51] Int. Cl.$^4$ .................. C12P 19/20; C12P 19/02
[52] U.S. Cl. .................................. 435/96; 435/99; 435/105
[58] Field of Search ................ 435/95, 96, 99, 105

[56] References Cited

U.S. PATENT DOCUMENTS

| | | |
|---|---|---|
| 2,583,451 | 1/1952 | Wallerstein et al. |
| 3,783,100 | 1/1974 | Larson et al. |
| 3,912,590 | 10/1975 | Slott et al. |
| 3,922,196 | 11/1975 | Leach et al. |
| 3,922,197 | 11/1975 | Leach et al. |
| 3,922,198 | 11/1975 | Kuske et al. |
| 3,922,199 | 11/1975 | Hebeda et al. |
| 3,922,200 | 11/1975 | Walon et al. |
| 3,922,201 | 11/1975 | Hebeda et al. |
| 4,009,074 | 2/1977 | Walon |
| 4,017,363 | 4/1977 | McMullen et al. |
| 4,092,434 | 5/1978 | Yoshizumi et al. |
| 4,113,509 | 9/1978 | Leach et al. |
| 4,159,982 | 7/1979 | Hermansson ............. 426/657 X |

OTHER PUBLICATIONS

Evers, A. D. et al., "Scanning Electron Microscopy of Wheat Starch", Die Starke 23, Jahrg., 1971, Hr. 1, pp. 16–18.
Walker, G. J., et al., "The Action of Some α-Amylases on Starch Granules", Biochem. J., 86, 1963, pp. 452–462.
Jones, C. R., "The Production of Mechanically Damaged Starch in Milling as a Governing Factor in the Diastatic Activity of Flour", Cereal Chem., vol. XVII, Mar., 1940, No. 2, pp. 133–169.
Sandstedt, R. M. et al., "Alpha-Amylase Adsorption on Raw Starch and its Relation to Raw Starch Digestion", J. Japan. Soc. of Starch Science, vol. 17, No. 1, 1969, pp. 215–228.

Primary Examiner—Robert Yoncoskie
Attorney, Agent, or Firm—Philip L. Bateman; James B. Guffey; Michael F. Campbell

[57] ABSTRACT

There is disclosed a process for enzymatically hydrolyzing a non-gelationized granular starch material directly to glucose. In another embodiment, granular starch remaining non-hydrolyzed following a direct, granular starch hydrolysis process and having liberated fat and/or protein residues coated, adsorbed or otherwise accumulated thereon is pasted, thinned separated from said fat and/or protein residues and recycled to said granular starch hydrolysis process for further hydrolysis to glucose therein.

13 Claims, No Drawings

PROCESS FOR THE ENZYMATIC HYDROLYSIS OF NON-GELATINIZED GRANULAR STARCH MATERIAL DIRECTLY TO GLUCOSE

BACKGROUND OF THE INVENTION

The present invention pertains in one aspect to a method of removing fat-protein residues from a starch hydrolysate solution containing same. In another aspect, such invention pertains to methods or processes for the hydrolysis of a granular starch material to glucose. In yet another aspect, this invention relates to a method for separating fat-protein residues from a granular starch material having said fat-protein residues adsorbed, coated or otherwise deposited upon the surface thereof and for converting said granular starch material to maltodextrin, syrups and/or glucose.

In the manufacture of starch hydrolysate materials such as maltodextrin, syrups, glucose, etc. from a granular starch feedstock, it is conventional practice to first subject an aqueous slurry of said granular starch material to a cooking or pasting operation, which is typically conducted at a temperature of from about 90° to about 180° C., and to thereafter convert the resulting cooked or pasted starch material to the desired starch hydrolysate product (e.g., typically maltodextrin, syrup or glucose) via one or more acid and/or enzyme hydrolysis operations.

In the case of enzyme-based hydrolysis operations, the cooked or pasted starch is typically treated for a relatively short period of time (e.g., 1 to 4 hours) under mildly acidic conditions (e.g., generally at a pH of about 6) and at a relatively high temperature (e.g., up to about 115° C.) with thermostable alpha-amylase enzyme in order to convert said starch slurry to maltodextrin. Such treatment is generally referred to in the art as the "thinning" reaction. In the event that the maltodextrin thus formed is the desired end-product, the crude hydrolysis reaction product is purified by removing the fat and/or protein (also referred to herein as fat-protein) liberated from the granular starch material during the cooking or pasting operation via a conventional separation technique such as filtration, centrifugation etc. The fat and/or protein material liberated and removed in this fashion is commonly referred to in the art as "mud".

On the other hand, if the desired ultimate end-product is syrup or glucose, the aforementioned maltodextrin material is subjected to further hydrolysis to convert said maltodextrin material (typically having a dextrose equivalent, D.E., of from about 1 to about 25 and preferably from about 5 to about 15) to the desired syrup or glucose product. This latter hydrolysis operation is commonly referred to in the art as a "saccharification" process or operation. When said saccharification operation is performed via acid hydrolysis techniques, it is typically conducted using a strong mineral acid such as hydrochloric or sulfuric acid; at a pH in the range of from about 1 to about 2; at a temperature in the range of from about 90° to about 180° C.; and for a time period or reaction time of from about 0.1 to about 2 hours. Alternatively, when said saccharification process is performed via an enzyme hydrolysis reaction, it is generally conducted using glucoamylase enzyme at a pH of about 4 to about 5; at a temperature of approximately 60° C.; and for a reaction period of from about 24 to about 96 hours.

In those instances wherein the maltodextrin material is further hydrolyzed to glucose or syrup, the removal of fat and/or protein materials released or liberated from the granular starch feedstock during the cooking operation and/or during the initial hydrolysis (e.g. "thinning") operation is conventionally conducted either prior to, during or after the maltodextrin-to-syrup or glucose hydrolysis operation using conventional separation techniques such as centrifugation, filtration and the like.

The foregoing techniques are generally capable of converting granular starch slurries to maltodextrin, syrup or glucose as desired and, indeed, they find relatively widespread commercial application for such purpose. However, such techniques are nonetheless still hampered by certain drawbacks or disadvantages. For example, the cooking or pasting operation and the initial starch-to-maltodextrin hydrolysis (or "thinning") operation are both conducted at relatively high temperatures and are therefore relatively energy intensive (and expensive) in character. In addition, the two different hydrolysis operations employed (i.e., starch-to-maltodextrin in the one instance and maltodextrin-to-syrup or glucose in the other) are generally conducted at different pH's and therefore require the addition of chemical reagents for pH adjustment purposes along with the attendant need to ultimately remove such reagents from the desired hydrolysate product. Moreover, the aforementioned maltodextrin-to-syrup or glucose enzyme hydrolysis operation (e.g., "saccharification" using glucoamylase enzyme at about 60° C. and a pH of about 4) is a relatively slow reaction requiring relatively long reaction times and thereby inherently placing significant limitations upon the ultimate production capacity of any given-sized manufacturing facility and/or reaction vessel. Accordingly, it would be highly desirable to provide a method for the hydrolysis of starch to maltodextrin, syrup and/or glucose which would minimize the aforementioned drawbacks and disadvantages.

In addition to the foregoing, it has also been observed that the conventional techniques (e.g., filtration and/or centrifugation) for removing liberated fat and/or protein during the aforementioned hydrolysis operations are oftentimes not as effective as might be desired in accomplishing their stated purpose and that, as a result, an undesired fat and/or protein build-up may occur over prolonged periods. This can be a highly undesirable development for several reasons. For example, the built-up fat and/or protein material may ultimately degrade within the saccharification reactor and the resulting degradation products may substantially reduce the quality of the desired starch hydrolysate product. Further, fat and/or protein in the saccharified product can foul ion exchange resins employed in downstream refining operations and can also cause the resulting hydrolysate product to be hazy or to have undesirable flavor components. Accordingly, it would be highly desirable to provide an improved method of removing fat and/or protein materials from starch hydrolysate solutions.

As an alternative to the above-described conventional starch hydrolysis methodology (i.e., involving first cooking or pasting a raw granular starch slurry feedstock followed by one or more subsequent enzyme and/or acid hydrolysis treatments), it has also been suggested to develop and employ enzyme hydrolysis processes capable of hydrolyzing a raw granular starch feedstock directly to maltodextrin and/or glucose at relatively low temperatures and without the starch feedstock first having been subjected to an initial cooking or pasting operation. See in this regard U.S. Pat. Nos. 3,922,196 and 3,922,197 to Leach et al.; 3,922,198 to Kuske et al.; 3,922,199 and 3,922,201 to Hebeda et al.; and 3,922,200 to Walon et al. (all of which issued on Nov. 25, 1975) for representative art pertaining to this latter technique or approach. Unfortunately, this type of approach is also not without certain drawbacks or disadvantages and is thought to have thus far not found commercial acceptance or applicability. For example, while certain enzyme systems have been proposed as being capable of directly hydrolyzing raw, granular starch material to maltodextrin, syrup and/or glucose, as a practical matter none proposed to date appear to have the capability of doing so at a commercially viable combination of yield, reaction rate and dry solids content. As such, it would be highly desirable to provide an efficient and effective method for the direct enzyme hydrolysis of a raw granular starch slurry feedstock to starch hydrolysate products such as maltodextrin, syrups, glucose and the like.

SUMMARY OF THE INVENTION

It has now been discovered that fat and/or protein contained in (or liberated from) starch hydrolysate solutions tend to adsorb, coat or otherwise become deposited on, or associated with, non-hydrolyzed, raw (e.g., uncooked and ungelatinized) granular starch material and that such material can therefore be suitably employed to facilitate or enhance the removal of said fat and/or protein from starch hydrolysate solutions containing same. Accordingly, one embodiment of the present invention is a process for removing liberated fat and/or protein residues from a starch hydrolysate solution containing same, said process comprising the steps of:

(a) contacting said starch hydrolysate solution with a granular starch material in an amount capable of adsorbing at least a substantial portion of said fat and/or protein residues from said starch hydrolysate solution and for a time sufficient to accomplish said substantial adsorption; and (b) separating the resulting fat and/or protein-containing granular starch material from said starch hydrolysate solution.

In addition, it has also been discovered that, in those instances wherein a granular starch slurry (especially in the case of relatively high solids starch slurries) is directly hydrolyzed by enzyme systems capable of doing so, fat and/or protein released from the hydrolyzed starch during the hydrolysis process can become adsorbed or deposited on (e.g., forming a fat and/or protein coating on) starch granules or particles remaining non-hydrolyzed during intermediate stages of the hydrolysis process and that said fat and/or protein coating can substantially impede or retard the direct enzyme hydrolysis of those non-hydrolyzed starch granules or particles which are so-coated with fat and/or protein. As a result, substantially complete hydrolysis of the starting granular starch feedstock within commercially practicable reaction times and enzyme concentrations is prevented and fat and/or protein-coated non-hydrolyzed granular starch material remains in the reaction mixture upon the practical completion of the direct enzyme hydrolysis operation and must be removed therefrom in order to recover the desired starch hydrolysate solution. Thus, the present invention in another of its embodiments is a process for the hydrolysis of a granular starch material comprising the steps of:

(a) partially hydrolyzing a granular starch slurry in a treatment (1) in which said starch slurry is contacted with an enzyme system capable of hydrolyzing starch in granular form directly to glucose, said enzyme being employed in an amount which, under the specific hydrolysis temperature and time employed, is sufficient to hydrolyze at least a substantial proportion (e.g. from about 50 to about 95, more typically from about 70 to about 90, weight percent) of said granular starch material to glucose but is insufficient to hydrolyze all of said starch material, and (2) in which fat and/or protein is liberated from the hydrolyzed starch material during said treatment and wherein said liberated fat and/or protein is adsorbed or deposited upon, or otherwise becomes associated with, starch granules remaining substantially non-hydrolyzed therein; and (b) thereafter separating the non-hydrolyzed granular starch material having fat and/or protein adsorbed or deposited thereon (or otherwise associated therewith) from the glucose syrup product resulting from the starch hydrolysis accomplished in step (a) and recovering said glucose syrup product.

In yet another of its embodiments, the present invention is a direct granular starch enzyme hydrolysis process as set forth above which further comprises a step in which the non-hydrolyzed granular starch material having liberated fat and/or protein residues adsorbed, coated or deposited thereon, or otherwise associated therewith, is treated so as to separate said non-hydrolyzed starch material from said fat and/or protein residue. Preferably, said non-hydrolyzed starch is ultimately converted to (i.e., recovered in the form of) starch hydrolysate products such as maltodextrin, syrup or glucose.

DETAILED DESCRIPTION OF THE INVENTION

As has been indicated, one embodiment of the present invention entails the use of granular starch material to remove fat and/or protein components from a starch hydrolysate solution containing same. Said embodiment makes use of the discovery that such fat and/or protein components tend to adsorb, deposit, or accumulate upon, or to otherwise become associated with, said granular starch material and, as such, said embodiment finds applicability in essentially any situation in which it is desired to separate fat and/or protein components from a starch hydrolysate solution containing same.

In practicing this particular embodiment of the invention, the starch hydrolysate solution containing fat and/or protein components to be removed therefrom is contacted with the granular starch material in any manner which is convenient or desired under the circumstances and for a time sufficient to adsorb (or to otherwise collect or capture) at least a substantial proportion of said fat and/or protein components. The resulting fat and/or protein-containing granular starch material is then separated from said starch hydrolysate solution.

Thus, for example, granular starch material can be added to and admixed, or agitated, with a quantity of the starch hydrolysate solution within a suitable tank, vat or similar vessel and can be subsequently separated from said starch hydrolysate solution using conventional solid/liquid separation techniques such as centrifugation, filtration or the like. Typically, a contact time of from about 15 minutes to about 2 hours (preferably from about 30 minutes to about 1 hour) will be suitable under such circumstances for the desired fat and/or protein removal purposes. Alternatively, said starch hydrolysate solution can be passed through a fixed or confined bed or filter cake of said granular starch material in order to remove the fat and/or protein components therefrom. In this latter instance said granular starch bed or filter cake can suitably be designed for periodic batch-wise replacement with fresh granular starch material or it can be designed and operated so as to continuously replace used fat and/or protein-saturated granular starch with fresh granular starch material. Naturally, contact time in this latter instance will generally be substantially shorter than that mentioned above and will typically be on the order of a few (e.g. 5 to 10) seconds to several (e.g. 5 or 10) minutes.

Typically, from about 0.05 to about 0.5 (preferably from about 0.1 to about 0.35) parts by weight of granular starch material will be employed for each part (on a dry solids basis) by weight of starch hydrolysate material being treated. Additionally, while the treatment temperature is not believed to be particularly critical, operation at a starch hydrolyzate temperature in the range of from about 25° to about 100° C. (especially from about 40° to about 65° C.) is generally convenient and preferred.

The present invention may be employed in any instance in which it is desired to remove liberated fat and/or protein residues from a starch hydrolysate solution. Thus, it is applicable to aqueous starch hydrolysate solutions derived from starch-containing feedstocks such as maize, wheat, sorghum, potatoes, tapioca and the like. Similarly, such invention is applicable regardless of the hydrolysis method by which said starch hydrolysate solution is initially prepared. Thus, for example, said invention may be suitably employed in connection with starch hydrolysate solutions which have been prepared in the conventional fashion by initially cooking or pasting a starch slurry and by subsequently subjecting the resulting cooked or pasted material to enzyme hydrolysis, acid hydrolysis or a combination thereof. In such instance, the treatment of the starch hydrolysate solution with granular starch to remove liberated fat and/or protein components in accordance with the present invention can be suitably accomplished at any stage of the hydrolysis operation after the cooked or pasted starch feedstock has been hydrolyzed to a maltodextrin material (i.e., a dextrose equivalent, D.E., of from 1 to about 25, preferably from about 5 to about 15) via acid or enzyme hydrolysis. That is, fat and/or protein removal in accordance with this invention can be accomplished either prior to, during or after the final acid or enzyme hydrolysis of said maltodextrin material to syrup or glucose. Indeed, in certain instances it may be desirable or advantageous to employ multiple granular starch treatments for maximum fat and/or protein removal effectiveness. In such event, for example, one such treatment may suitably be employed immediately following the hydrolysis of the cooked or pasted starch material to maltodextrin (e.g., using acid hydrolysis, alpha-amylase enzyme hydrolysis, etc.) and another employed for further fat and/or protein removal following the subsequent hydrolysis of said maltodextrin to syrup or glucose (e.g., using glucoamylase hydrolysis, acid hydrolysis, or the like).

In one particularly preferred embodiment, the present invention is employed in connection with a starch hydrolysis process in which raw (non-gelatinized) granular starch is directly hydrolyzed to glucose by enzyme hydrolysis (i.e., without a cooking or pasting operation and without an intermediate "thinning" step for the hydrolysis of starch to maltodextrin). In such process, an aqueous granular starch slurry, typically having a starch solids content in excess of about 20 weight percent (and preferably in the range from about 25 to about 35 weight percent) on a total slurry weight basis, is contacted with an enzyme system capable of directly hydrolyzing granular starch to glucose. Preferably such direct hydrolysis is conducted at a temperature of from about 50° to about 65° C., at a pH of from about 5.0 to about 7 (preferably from about 5 to about 6.5) and for a time period of from about 24 to about 96 (preferably from about 24 to about 72) hours.

An especially preferred enzyme system for use in said process is one derived from a fungal organism which is a strain of the genus Humicola (most preferably *Humicola grisea* var. *thermoidea*) and the amount of enzyme employed is typically from about 5 to about 60 10 D.E. units per gram of dry starch solids wherein a "10 D.E. unit" is as hereinafter defined in connection with Example 1 hereof.

During the aforementioned direct enzyme hydrolysis operation, a substantial proportion, but less than all, of the granular starch material is hydrolyzed directly to glucose (thereby forming an aqueous glucose solution or syrup) and fat and/or protein is liberated from the hydrolyzed starch material in the process. Also in said process, the liberated fat and/or protein material is adsorbed or deposited onto, or otherwise becomes associated with, those starch granules remaining non-hydrolyzed therein and the resulting fat and/or protein-containing granular starch material is subsequently separated from the resulting aqueous glucose solution or syrup via centrifugation, filtration or other conventional solids/liquid separation technique.

The fat and/or protein-containing granular starch material recovered in the foregoing fashion can be further handled or disposed of in a variety of ways. Said material can, for example, be employed without further hydrolysis treatment to prepare various animal feed products and the like. Alternatively and preferably, however, such fat and/or protein-containing granular starch material is further treated so as to remove the fat and/or protein therefrom and so as to ultimately recover the starch value thereof in the form of a starch hydrolysate product such as maltodextrin, syrup or glucose.

In the latter event, several alternatives are available for the further treatment to separate the fat and/or protein from the granular starch material with which it is associated and to hydrolyze same to maltodextrin, syrup or glucose as desired. However, (and as has been noted previously), said fat and/or protein has been found to substantially impair or retard the ability of the aforementioned enzyme system to directly hydrolyze said starch granules to glucose within a commercially practicable time period. As such, simply subjecting the indicated fat and/or protein-coated granular starch material to further direct enzyme hydrolysis treatment (e.g., such as by directly recycling same to the aforementioned direct enzyme hydrolysis operation from which it was recovered or by directly subjecting same to a similar but separate direct enzyme hydrolysis treatment) does not generally constitute a viable means for converting said fat and/or protein-coated starch material to the desired starch hydrolysate product. Accordingly, if it is desired to hydrolyze the indicated fat and/or protein-coated granular starch material using a granular starch enzyme hydrolysis treatment as described above, it is generally necessary to first remove the fat and/or protein coating therefrom via a suitable separation treatment means (such as, for example, solvent extraction, lipase/protease treatment and separation, surfactant addition followed by floatation separation; and the like) prior to said direct granular starch enzyme hydrolysis treatment of said granular starch material.

One notable exception to the foregoing involves a finding that, even in spite of the aforementioned fat and/or protein coating, direct enzyme hydrolysis as described above can be effectively accomplished without the necessity of first removing such fat and/or protein coating from the granular starch material containing same if said direct enzyme hydrolysis is conducted upon an aqueous slurry of said granular starch material at a relatively low solids level (e.g., below 20 weight percent, and preferably about 16 weight percent or less, granular starch on a total slurry weight basis). Accordingly, in one particularly preferred embodiment within the general scope of the present invention, the aforementioned fat and/or protein-coated remaining or residual granular starch material is recovered and converted to a starch hydrolysate material (e.g., glucose) by subjecting same, in granular form, to direct enzyme hydrolysis at a granular starch solids level below 20 weight percent (preferably about 16 weight percent or less) on a total slurry weight basis. Thus, when this latter residual starch recovery technique is employed, the overall starch hydrolysis process which results is a multiple-step process for solubilizing and saccharifying a granular starch material in which a substantial proportion (e.g. 60 percent or more), but less than all, of a relatively high solids (e.g., from about 20 to about 60 percent starch on a total slurry weight basis) aqueous granular starch slurry is hydrolyzed directly to glucose in a first step using a raw starch hydrolyzing enzyme at a pH of from about 5 to about 7.0 and at a temperature of from about 50° to about 65° C. and in which substantially all of the remainder of the granular starch in said slurry is hydrolyzed directly to glucose in a second step (following separation of said remaining granular starch material from the first step syrup and re-slurrying of said starch material to form a second slurry) which is conducted, using a raw starch hydrolyzing enzyme within the same temperature and pH ranges as noted above for the first step of the process, upon a relatively low solids content (i.e., less than 20 weight percent, and preferably about 16 weight percent or less on a dry starch solids basis) second aqueous granular starch slurry.

Another particularly preferred method in accordance with the present invention for treating the residual non-hydrolyzed, fat and/or protein-containing granular starch material to recover the starch value therefrom is a first cook or paste same at a temperature of at least about 80° C.; to thereafter hydrolyze the resulting cooked or pasted material to maltodextrin (e.g., D.E. of 1 to about 25, preferably from about 5 to about 15) via conventional acid or enzyme hydrolysis (e.g., a conventional "thinning" operation); and to subsequently purify the resulting maltodextrin material by removing therefrom (e.g., by filtration, centrifugation, etc.) the fat and/or protein components which are released during the preceding cooking and hydrolysis processing steps.

The maltodextrin material recovered in the foregoing fashion may be used as such in a variety of known applications such as, for example, bases for food items; bodying agents; carriers for synthetic sweeteners; flavor enhancers; coloring agent additives; spray drying adjuncts for coffee or tea extracts; bulking or bodying agents for synthetic creams or coffee whiteners; moisture holding agents in breads, pastries, meats, etc.; bodying and smoothing agents in puddings, soups, frozen desserts, etc. and the like. Alternatively, said material may be further hydrolyzed to glucose via acid or enzyme hydrolysis. Such further hydrolysis (or "saccharification") can suitably be conducted in a hydrolysis operation which is separate from the hereinbefore discussed direct hydrolysis operation (i.e., in which uncooked granular starch is directly enzyme hydrolyzed to glucose and in which the fat and/or protein-containing granular starch being treated in this instance was initially generated). In such event, said further hydrolysis can suitably be conducted using the hereinbefore discussed acid or enzyme hydrolysis (or saccharification) techniques. In the latter case the enzyme system employed can be either one which is capable of substantially complete hydrolysis of both maltodextrin and uncooked granular starch to syrup or glucose under commercially practicable reaction conditions (e.g., such as at a solids content of at least about 20 weight percent; at a pH of from about 5.0 to about 6.0, especially about 5.5; at a temperature of from about 55° C. to about 60° C.; and during a reaction time of no more than about 96 hours) or one which, under conventional enzyme saccharification conditions and during a comparable reaction period, is capable of substantially complete hydrolysis of maltodextrin to syrup or glucose but incapable of substantially complete direct hydrolysis of uncooked granular starch to syrup or glucose. As used herein, "substantially complete hydrolysis" means that at least about 94 percent of the initial quantity of the original maltodextrin or granular starch substrate is converted to syrup or glucose product. Preferably, however, the further hydrolysis of this recovered maltodextrin material is conducted by recycling said maltodextrin material to that stage of the overall process or operation in which the initial granular starch-to-glucose direct enzyme hydrolysis is conducted and thereby hydrolyzing fresh granular starch feed material and the recycled maltodextrin material to glucose simultaneously in the same processing step.

The present invention is further illustrated by reference to the following examples thereof in which all ratios, parts and percentages are on a weight basis unless otherwise specified.

EXAMPLE 1

Granular starch containing on a dry substance basis (dsb), about 0.59 weight percent protein (as reflected by a nitrogen content of 0.095 weight percent) and 0.39 weight percent fat is slurried in water to form a slurry containing about 26 weight percent (dsb) of starch solids on a total slurry weight basis. To said slurry is also added 100 parts per million (ppm) calcium ion (in the form of calcium chloride) and 15 10 D.E. units per gram of dry starch solids of a raw starch hydrolase enzyme preparation produced by the fungus *Humicola grisea* var. *thermoidea*, wherein one "10 D.E." unit corresponds to the amount of said enzyme which will produce 1μ mole of glucose per minute when added to a 2% dry solids (ds) maltodextrin syrup having a dextrose equivalent (DE) of 10 at 50° C. and pH 5.5 over a 10 minute reaction period.

The resulting starch slurry/enzyme mixture is then heated to 55° C. and the pH thereof is adjusted to a value of 6 and said mixture is maintained at the indicated pH and temperature conditions (with stirring) for a reaction period of 4 days. At the end of said reaction period, the granular starch solids remaining unhydrolyzed are separated from the resulting liquid glucose syrup phase by filtration; reslurried in water; filtered again; and air dried. Approximately 88 weight percent of the initially charged granular starch material is found to have been hydrolyzed to glucose and the resulting glucose syrup contains, on a total weight basis, approximately 26.5 weight percent dissolved solids, of which about 96 weight percent is glucose. On a dry solids basis, said syrup is found to contain 0.082 weight percent nitrogen and 0.055 weight percent fat.

The remainder (i.e., about 12 weight percent) of the initially charged granular starch material remains in solid, insoluble, unhydrolyzed form and is found to contain about 1.16 weight percent protein (as reflected by a measured nitrogen content of 0.185 weight percent) and about 2.93 weight percent fat. Thus, it is apparent that fat and protein liberated from the starch upon hydrolysis to glucose is adsorbed on (or otherwise collected) by that portion of the granular starch remaining unhydrolyzed during the hydrolysis operation.

EXAMPLE 2

In this example, granular starch containing, on a dry substance basis, 0.75 weight percent protein and 0.29 weight percent fat is admixed with water to form a slurry containing 33 weight percent starch on a total slurry weight basis and the resulting slurry is agitated overnight at a pH of 5.5 and at a temperature of 60° C. Thereafter, 0.275 weight percent (on a dry substance starch basis) each of Termamyl 60 L alpha-amylase enzyme and Miles Diazyme L-100 glucoamylase enzyme are added to said slurry and the hydrolysis reaction is permitted to proceed, with stirring, for a reaction period of 72 hours at a pH of 5.5 and at 60° C.

At the end of the reaction period, granular starch material remaining non-hydrolyzed is separated from the liquid glucose syrup phase of the reaction mixture by filtration.

Analysis of the glucose syrup and unhydrolyzed granular starch material recovered shows that approximately 72 percent of the initially charged granular starch has been hydrolyzed and that the resulting glucose syrup contains, on a total weight basis, about 29.7 weight percent solids of which 96.2 weight percent is glucose.

The residual granular starch remaining unhydrolyzed following the reaction is found to have a fat content of 0.81 weight percent and protein content of 1.50 weight percent, which represents fat and protein contents which are 280% and 200%, respectively, of the initial fat and protein contents of the originally charged granular starch material. Here again, accumulation of fat and protein components liberated during the hydrolysis reaction upon granular starch remaining unhydrolyzed therein is readily apparent.

Observation and reaction mixture analysis during the course of the hydrolysis reaction indicates that almost all of the granular starch-to-glucose hydrolysis takes place within the first 48 hours of the reaction and that very little further starch-to-glucose conversion takes place within the last 24 hours of the process.

EXAMPLE 3

An aqueous granular starch slurry containing 36 weight percent starch solids on a total weight basis is charged to a reactor vessel along with a raw starch hydrolase enzyme preparation produced by the fungus *Humicola grisea* var. *thermoidea*. The granular starch in said slurry contains, in weight percent on a dry solids basis (dsb), about 0.43% fat and about 0.31% protein (as reflected by a measured weight percent dsb nitrogen content of 0.05). The amount of enzyme employed is 15 10 D.E. units per gram of dry starch solids, wherein one "10 D.E." unit is as defined in Example 1 above.

The resulting starch slurry/enzyme mixture is then heated to 55° C. and the pH thereof is adjusted to a value of 6 and said mixture is maintained at the indicated pH and temperature conditions (with stirring) for a reaction period of 48 hours. At the end of said reaction period approximately 65 percent of the initially charged granular starch material has been hydrolyzed to glucose so as to form an aqueous glucose syrup phase containing approximately 29 weight percent dissolved solids on a total weight basis and in which approximately 96 weight percent of said dissolved solids is glucose. On a dry solids basis, said syrup is found to contain 0.03 weight percent fat and 0.06 weight percent nitrogen in the form of soluble nitrogen-containing protein hydrolysis products. Thus, the particular enzyme preparation employed in this example apparently contains enzyme species capable of hydrolyzing protein to lower molecular weight hydrolysis products.

The remainder (i.e., about 35 percent) of the initially charged granular starch material is separated from the syrup by filtration and is found to remain in solid, insoluble, unhydrolyzed granular form and to contain substantially higher fat and protein content than it had initially (i.e., from about 1.4 to about 1.9 times its initial fat content) and about the same (or somewhat less) protein content as it had initially.

In order to recover the starch value from the 35 weight percent portion of the initially charged granular starch material remaining unhydrolyzed and to separate same from the fat adsorbed or deposited thereon during the preceding granular starch hydrolysis process, the granular starch material receovered in the aforementioned filtration step is admixed with water to form a 30 weight percent solids (total weight basis) aqueous slurry and is cooked and thinned to a maltodextrin syrup at 100° C., at a pH of 5.9 and in the presence of 0.1% (on dry starch solids weight basis) Novo Termamyl 120 L Brand bacterial alpha amylase for a period of 30 minutes. Thereafter, the pH of the resulting maltodextrin syrup is adjusted to 4.5. Upon standing, fat and protein constituents liberated from the starch during the cooking and thinning operations float to the top of the reaction vessel and are separated from the maltodextrin syrup by centrifugation. The resulting maltodextrin syrup thereby recovered contains about 0.01 weight percent (dsb) nitrogen (reflective of a protein content of 0.0625 weight percent dsb) and about 0.7 weight percent (dsb) fat.

EXAMPLE 4

In this example, the procedure of Example 3 above is repeated except that the maltodextrin syrup recovered in the second part of Example 3 is recycled into the raw or granular starch hydrolysis reaction step along with a fresh feedstream of an aqueous granular starch slurry. Thus, the reactor charge in this instance comprises approximately 65 weight percent on a dry solids weight basis (dsb) of non-hydrolyzed granular starch material, about 35 weight percent dsb of the indicated maltodextrin syrup recycle and sufficient water to cause the resulting granular starch/maltodextrin syrup slurry to have a total dry solids content of about 36 weight percent on a total slurry weight basis along with the amount and type of raw starch hydrolysis enzyme indicated in Example 3 above.

The results obtained in this example are substantially the same as those in Example 3 in terms of the amount and quality of glucose syrup recovered from the raw starch hydrolysis reaction step itself; the amount of non-hydrolyzed elevated fat and protein-containing residual granular starch material remaining following said step; and in terms of the amount and character of maltodextrin syrup recovered following cooking, thinning and centrifugation of said residual granular starch material.

While the present invention has been described and illustrated herein with reference to certain specific embodiments and examples thereof, such fact is not to be interpreted as in any way limiting the scope of the instantly claimed invention.

What is claimed is:

1. A process for the hydrolysis of a non-gelatinized granular starch material comprising the steps of:
    (a) partially hydrolyzing a non-gelatinized granular starch slurry at a temperature which is from about 50° to about 65° C. and which is less than the gelatinization temperature of said granular starch material in a treatment (1) in which said starch slurry is contacted with an enzyme system capable of hydrolyzing starch in non-gelatinized granular form directly to glucose, said enzyme being employed in an amount which, under the specific hydrolysis temperature and time employed, is sufficient to hydrolyze at least a substantial proportion of said non-gelatinized granular starch material to glucose but is insufficient to hydrolyze all of said starch material, and (2) in which fat and/or protein is liberated from the hydrolyzed starch material during said treatment and wherein said fat and/or protein is adsorbed or deposited upon, or otherwise becomes associated with, non-gelatinized starch granules remaining substantially non-hydrolyzed therein; and
    (b) thereafter separating the non-hydrolyzed granular starch material having fat and/or protein adsorbed or deposited thereon or otherwise associated therewith from the glucose product resulting from the starch hydrolysis accomplished in step (a) and recovering said glucose product.

2. The process of claim 1 which further comprises a step (c) in which the non-hydrolyzed granular starch material having fat and/or protein adsorbed or deposited thereon or otherwise associated therewith is treated so as to separate said fat and/or protein material therefrom.

3. The process of claim 2 wherein separation of said non-hydrolyzed starch material from said fat and/or protein material is accomplished by:
    (a) cooking a slurry of said fat and/or protein containing starch material at a temperature of at least about 80° C.;
    (b) hydrolyzing said starch material sufficiently to form maltodextrin therefrom; and
    (c) separating the resulting maltodextrin material from the fat and/or protein materials which are liberated during said cooking and/or hydrolyzing operations.

4. The process of claim 3 wherein at least a portion of said maltodextrin material is subsequently converted to glucose by acid or enzyme hydrolysis.

5. The process of claim 4 wherein said maltodextrin hydrolysis to glucose is accomplished by recycling said maltodextrin material to that stage of the process in which the granular starch-to-glucose direct enzyme hydrolysis is conducted and hydrolyzing both granular starch feed material and the recycled maltodextrin to glucose simultaneously in the same processing step.

6. The process of claim 4 wherein the maltodextrin-to-glucose hydrolysis operation is conducted in a processing step separate from that in which the direct granular starch-to-glucose hydrolysis operation is conducted.

7. The process of claim 6 wherein the maltodextrin-to-glucose hydrolysis is accomplished using an enzyme system which is capable of substantially complete hydrolysis of maltodextrin to glucose at a pH of from about 4.0 to about 5.0, at a temperature of about 60° C. and during a reaction period of from about 24 to 96 hours but which is incapable of substantially complete direct hydrolysis of granular starch to glucose.

8. The process of claim 6 wherein the maltodextrin-to-glucose hydrolysis is accomplished using an enzyme system which is capable of substantially complete hydrolysis of both granular starch and maltodextrin to glucose at a pH of from about 5.0 to about 6.0, at a temperature of from about 55° to about 60° C. and during a reaction period of about 96 hours or less.

9. The process of claim 4 wherein the dextrose equivalent (D.E.) of the maltodextrin material to be hydrolyzed is from about 1 to about 25.

10. The process of claim 4 wherein the dextrose equivalent (D.E.) of the maltodextrin material to be hydrolyzed is from about 5 to about 15.

11. The process of claim 1 wherein the granular starch slurry to be hydrolyzed in step (a) thereof has a granular starch solids content in excess of about 20 weight percent on a total starch slurry weight basis.

12. The process of claim 1 wherein said direct granular starch-to-glucose hydrolysis of step (a) is conducted for a hydrolysis reaction time period of from about 24 hours to about 96 hours.

13. The process of claim 1 wherein the hydrolysis of step (a) is conducted (1) at a starch solids content in excess of 20 weight percent on a total slurry weight basis; (2) at a pH of from about 5.0 to about 7.0; and (3) for a time period of from about 24 to about 72 hours.

* * * * *